US011475571B2

(12) United States Patent
Kuroda et al.

(10) Patent No.: US 11,475,571 B2
(45) Date of Patent: Oct. 18, 2022

(54) APPARATUS, IMAGE PROCESSING APPARATUS, AND CONTROL METHOD

(71) Applicant: CANON KABUSHIKI KAISHA, Tokyo (JP)

(72) Inventors: Tomoki Kuroda, Tokyo (JP); Yoshikazu Kawai, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/808,245

(22) Filed: Mar. 3, 2020

(65) Prior Publication Data

US 2020/0294236 A1    Sep. 17, 2020

(30) Foreign Application Priority Data

Mar. 13, 2019  (JP) .............................. JP2019-045955
Feb. 14, 2020  (JP) .............................. JP2020-023378

(51) Int. Cl.
*G06T 7/00* (2017.01)
*G06T 7/62* (2017.01)
*A61B 5/00* (2006.01)

(52) U.S. Cl.
CPC .......... *G06T 7/0016* (2013.01); *A61B 5/0077* (2013.01); *A61B 5/447* (2013.01); *G06T 7/62* (2017.01); *A61B 2576/00* (2013.01); *G06T 2207/30092* (2013.01)

(58) Field of Classification Search
CPC . A61B 2576/00; A61B 5/0037; A61B 5/0077; A61B 5/1075; A61B 5/445; A61B 5/447; A61B 5/6898; A61B 5/743
See application file for complete search history.

(56) References Cited

U.S. PATENT DOCUMENTS

| 2001/0047126 | A1* | 11/2001 | Nagai | .................... G16H 40/63 600/300 |
| 2004/0212703 | A1* | 10/2004 | Sugimoto | .............. H04N 5/361 348/241 |
| 2011/0087110 | A1* | 4/2011 | Nathan | .................. A61B 5/415 600/476 |
| 2011/0115967 | A1* | 5/2011 | Lee | .................. H04N 5/232133 348/349 |

(Continued)

FOREIGN PATENT DOCUMENTS

| CN | 106485691 A | 3/2017 |
| CN | 108606782 A | 10/2018 |

(Continued)

OTHER PUBLICATIONS

JSPU Guidelines for the Prevention and Management of Pressure Ulcers (4th Ed ), Guidebook for Pressure Ulcers, Second Edition, Japanese Society of Pressure Ulcers, 2015, p. 23.

*Primary Examiner* — Md N Haque
(74) *Attorney, Agent, or Firm* — Canon U.S.A., Inc. IP Division

(57) ABSTRACT

An apparatus includes a sensor configured to capture an image of an affected part, and a processor configured to obtain information about a size of the affected part in the captured image, and control timing to capture an image of the affected part or control timing to prompt a user to perform an imaging operation based on the information about the size of the affected part.

8 Claims, 10 Drawing Sheets

(56) References Cited

U.S. PATENT DOCUMENTS

| | | | | |
|---|---|---|---|---|
| 2011/0228128 A1* | 9/2011 | Ikeda | ............ | G03B 7/097 |
| | | | | 348/222.1 |
| 2012/0155707 A1* | 6/2012 | Kawano | ............ | G06K 9/00342 |
| | | | | 382/103 |
| 2013/0057714 A1* | 3/2013 | Ishii | ............ | H04N 5/23248 |
| | | | | 348/208.4 |
| 2016/0175615 A1* | 6/2016 | Yanagawa | ............ | G06T 7/248 |
| | | | | 382/103 |
| 2016/0379370 A1* | 12/2016 | Nakazato | ............ | G01B 11/24 |
| | | | | 382/103 |
| 2017/0004625 A1* | 1/2017 | Kamiyama | ............ | G06T 7/0016 |
| 2017/0132784 A1* | 5/2017 | Yamada | ............ | G06T 7/74 |
| 2017/0147789 A1 | 5/2017 | Wiedenhoefer | | |

FOREIGN PATENT DOCUMENTS

| | | |
|---|---|---|
| CN | 108737631 A | 11/2018 |
| CN | 108742671 A | 11/2018 |
| CN | 108875648 A | 11/2018 |
| CN | 109223303 A | 1/2019 |

\* cited by examiner

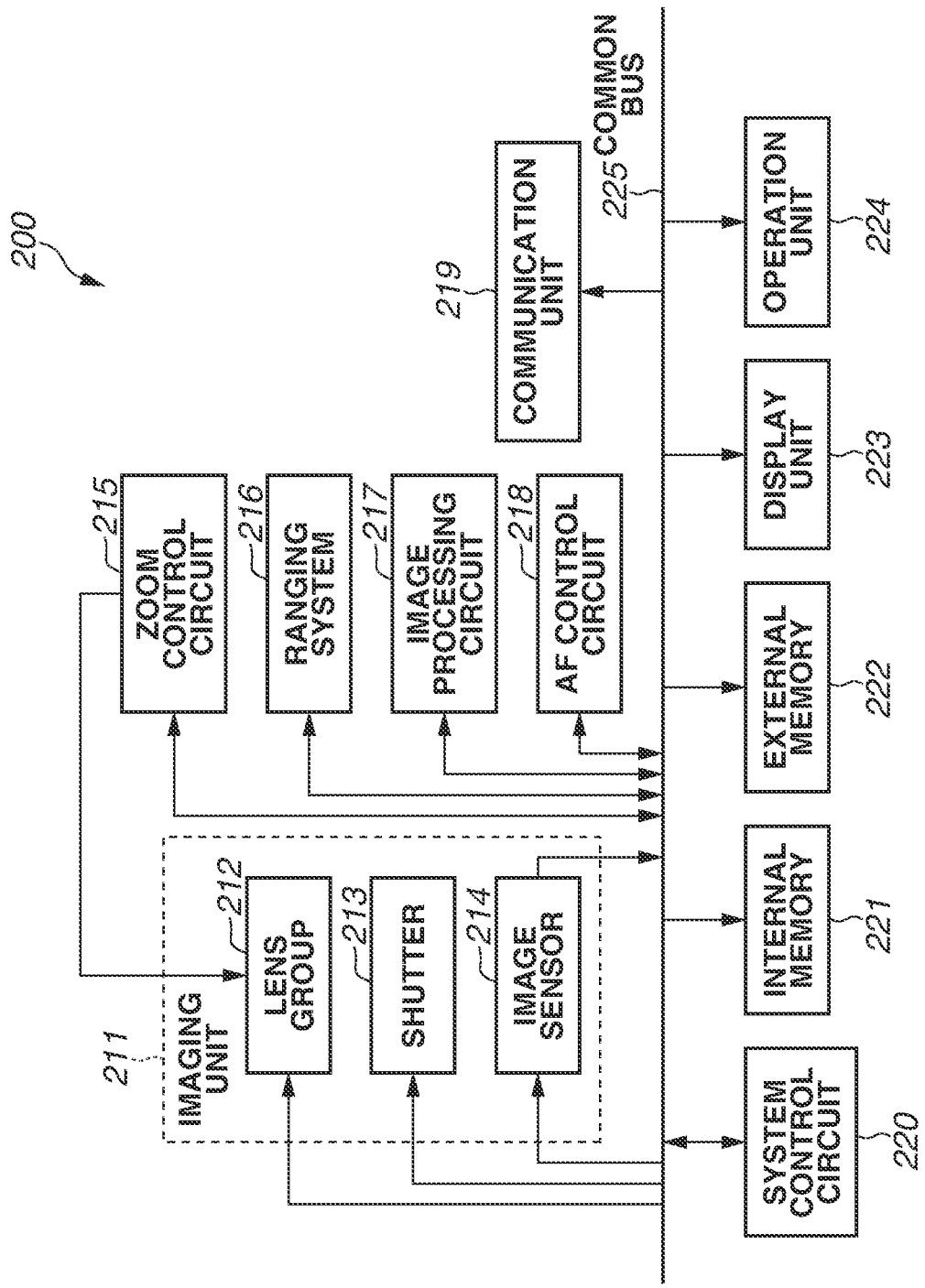

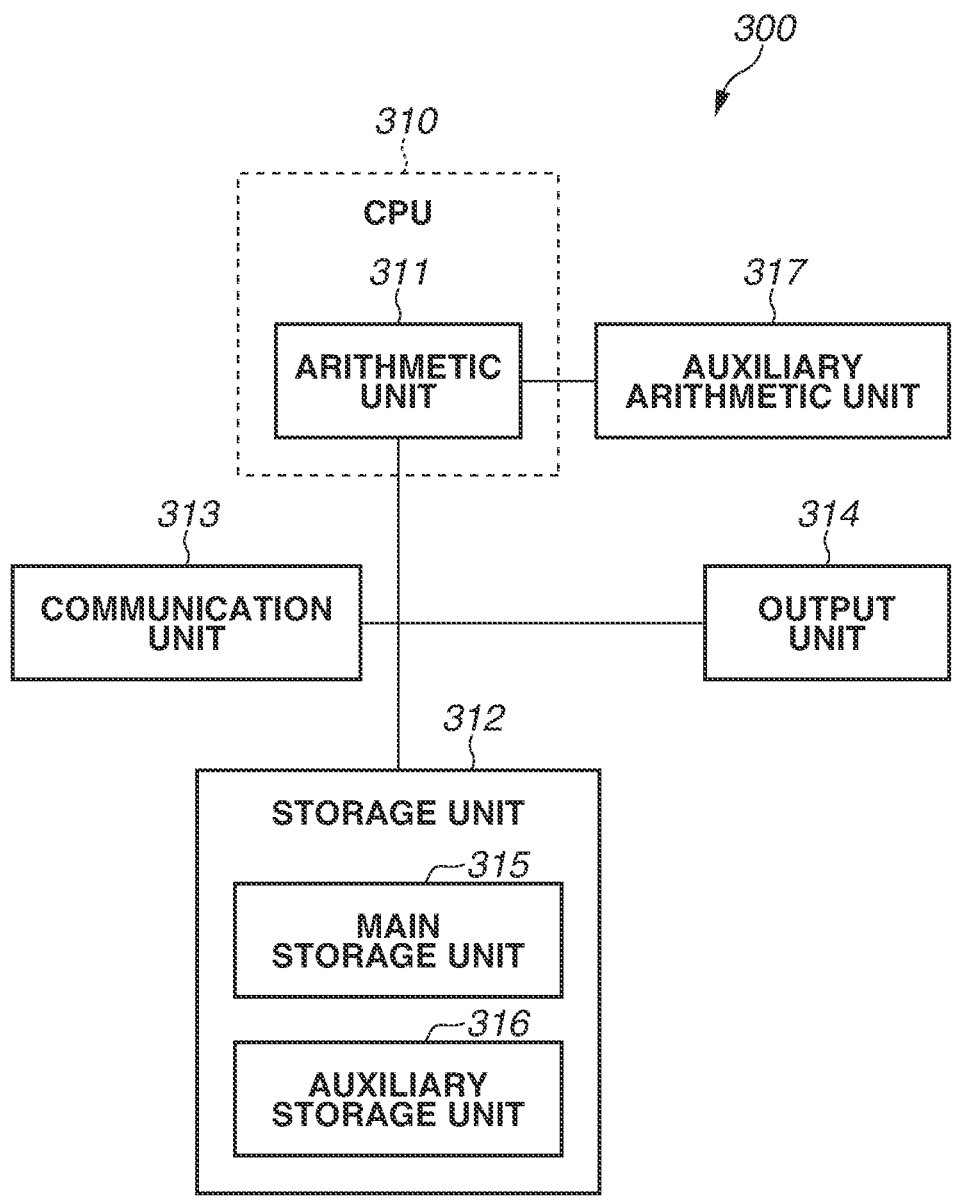

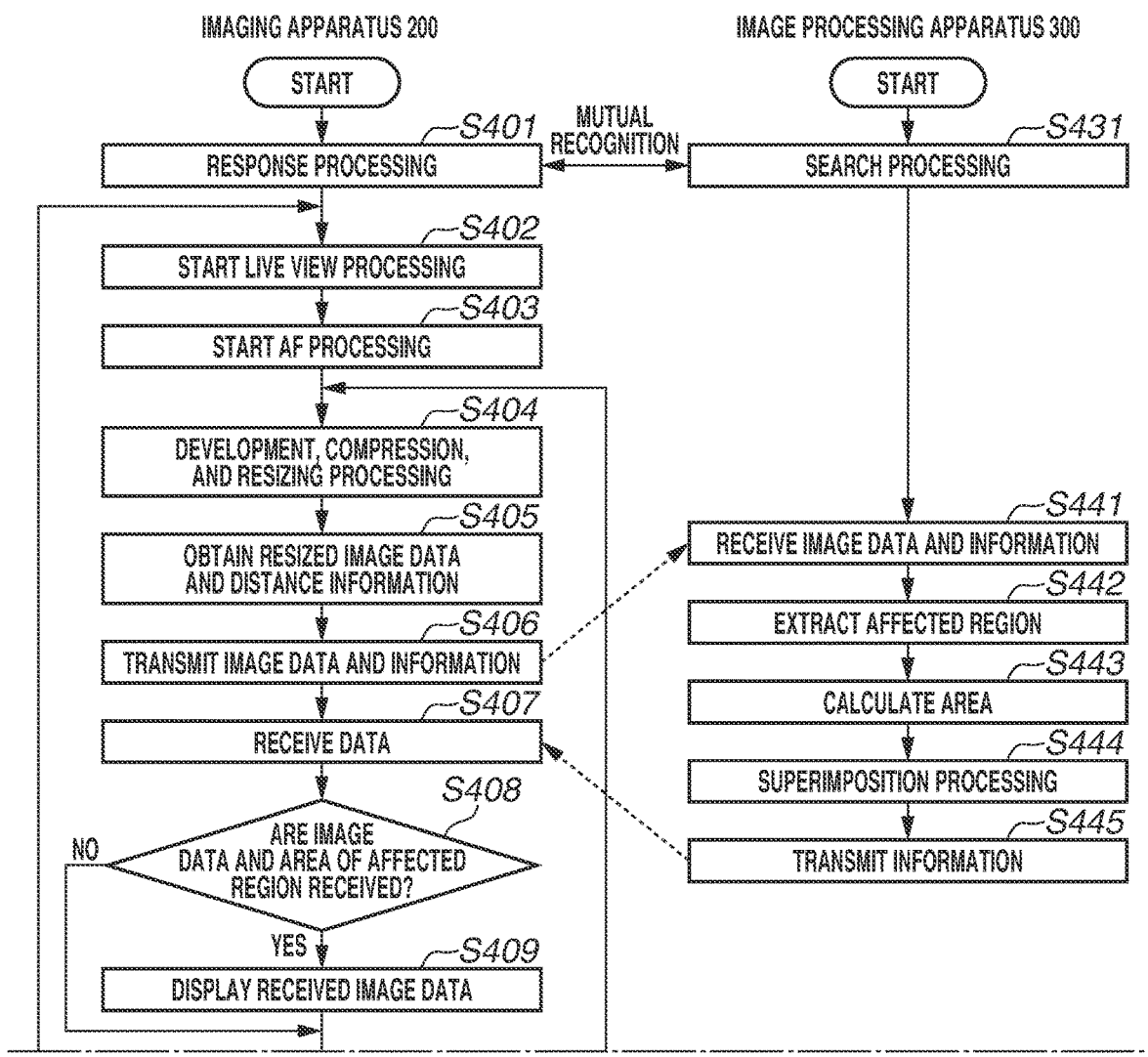

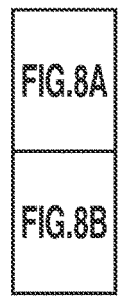
FIG.8
FIG.8A
FIG.8B
FIG.8A
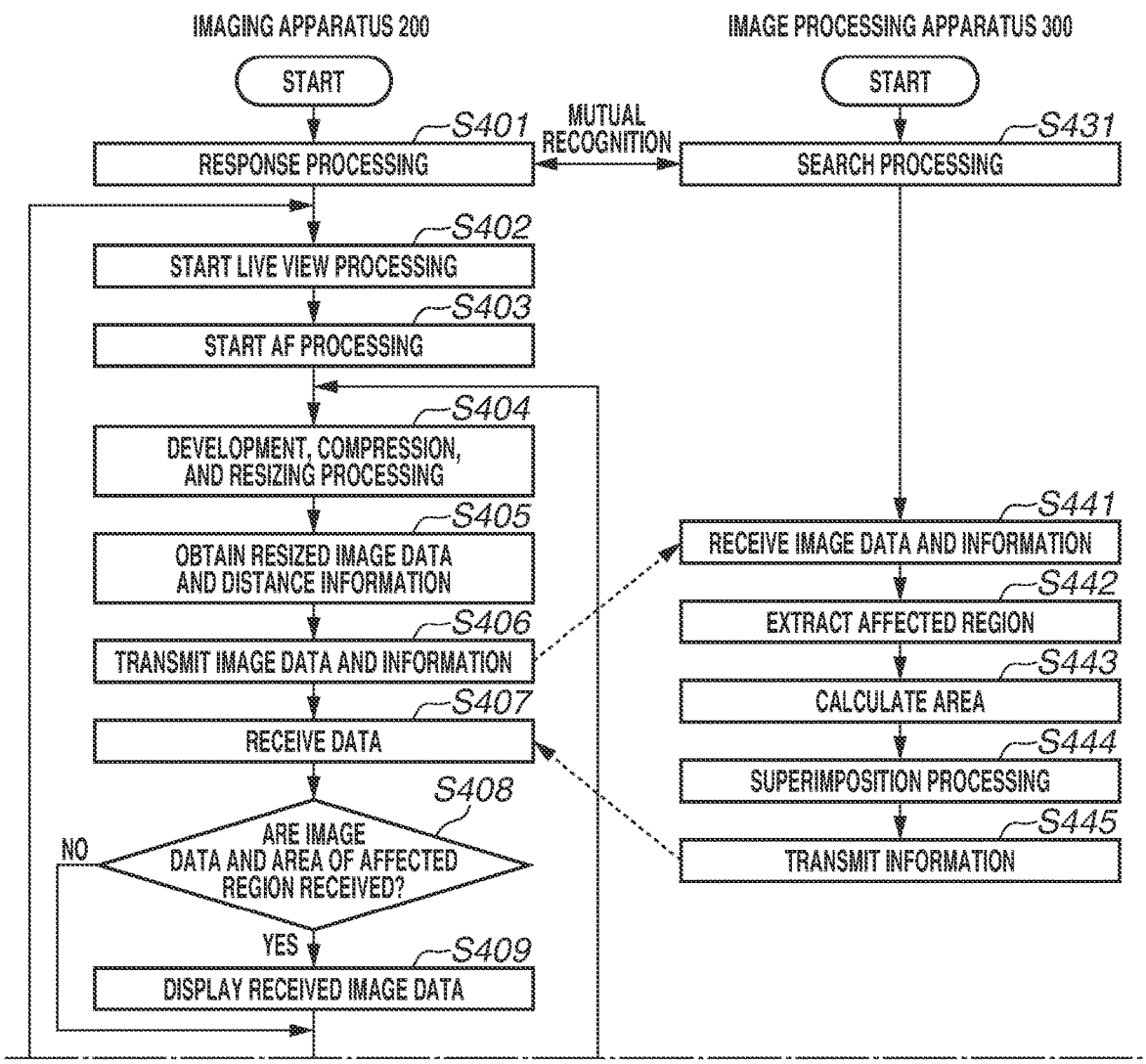

APPARATUS, IMAGE PROCESSING APPARATUS, AND CONTROL METHOD

BACKGROUND OF THE INVENTION

Field of the Invention

The aspect of the embodiments relates to an apparatus, an image processing apparatus, and a control method.

Description of the Related Art

Humans and animals in a lying position can develop pressure ulcers or bedsores because a part of the body is pressed against the supporting surface in contact with the body due to the body weight. Provision of pressure ulcer treatment such as body pressure dispersion care and skin care to patients developing pressure ulcers may be desirable, along with regular evaluation and management of the pressure ulcers.

DESIGN-R (registered trademark), a pressure ulcer status assessment scale developed by the Scientific Education Committee of the Japanese Society of Pressure Ulcers, is discussed as a pressure ulcer evaluation tool in "Guidebook for Pressure Ulcers", 2nd Ed., compliant with JSPU Guidelines for the Prevention and Management of Pressure Ulcers (4th Ed.), (edited by the Japanese Society of Pressure Ulcers, International Standard Book Number (ISBN)-13 978-4796523608), Shorinsha, p. 23. DESIGN-R is a tool for evaluating the healing process of wounds including pressure ulcers. This scale is named after the acronym of observation items: depth, exudate, size, inflammation/infection, granulation, and necrotic tissue.

There are two types of DESIGN-R scale, one for severity classification intended for daily simple evaluation and one for monitoring that indicates the course of healing process in detail. DESIGN-R for severity classification includes six evaluation items, each including two classifications: slight and serious. Classifications "slight" are indicated by lower-case letters, and "serious" by upper-case letters.

At initial treatment, the rough status of a pressure ulcer can be found out by making an evaluation using DESIGN-R for severity classification. The course of treatment can be easily determined since it can be understood which item or items the issue is related to by the evaluation.

DESIGN-R capable of severity comparison between patients in addition to monitoring has also been developed for monitoring purposes. "R" stands for rating (evaluation, scoring). The items are given respective different weights, and the total score (0 to 66 points) of six items except depth indicates the severity of the pressure ulcer. After start of treatment, the course of treatment can be evaluated in detail and in an objective manner, which enables not only individual monitoring but a severity comparison between patients as well.

According to DESIGN-R, size is evaluated by measuring the major axis and the minor axis (longest diameter orthogonal to the major axis) of a skin wound area (in units of cm). Size that is a numerical value obtained by multiplying the measurements of the major and minor axes is classified in seven grades. The seven grades include the following: s0: none; s3: smaller than 4 $cm^2$; s6: 4 $cm^2$ or larger, but smaller than 16 $cm^2$; s8: 16 $cm^2$ or larger, but smaller than 36 $cm^2$; s9: 36 $cm^2$ or larger, but smaller than 64 $cm^2$; s12: 64 $cm^2$ or larger, but smaller than 100 $cm^2$; and s15: 100 $cm^2$ or larger.

As discussed in the foregoing Guidebook for Pressure Ulcers, DESIGN-R scores are recommended to be assessed once a week or two weeks for evaluation of the healing process of pressure ulcers and appropriate care selection. For pressure ulcers, regular status assessment and management may be desirable. To observe a change in the status of a pressure ulcer, high evaluation accuracy is demanded.

Under the circumstances, the size of a pressure ulcer is often evaluated based on values manually measured by putting a measuring tape over the affected part. Specifically, the longest straight distance between two points in the skin wound area is measured as a major axis. The length orthogonal to the major axis is measured as a minor axis. The measurements of the major and minor axes are multiplied to determine the size of the pressure ulcer.

In capturing an image of a pressure ulcer, the bedridden patient is half raised and the photographer takes an unnatural posture to capture an image of the back. Appropriate images can therefore fail to be captured. Since the shape and area of a pressure ulcer vary depending on the patient's position, the pressure ulcer can appear differently each time an image is captured. Accurate comparison of the progress of the pressure ulcer using captured images of the pressure ulcer is therefore difficult. Such an issue is not limited to pressure ulcers but also applies to imaging of burns and lacerations.

SUMMARY OF THE INVENTION

The aspect of the embodiments is directed to appropriately capturing an image of the affected part.

According to an aspect of the embodiments, an apparatus includes a sensor configured to capture an image of an affected part, and a processor configured to obtain information about a size of the affected part in the captured image, and control timing to capture an image of the affected part or control timing to prompt a user to perform an imaging operation based on the information about the size of the affected part.

Further features of the disclosure will become apparent from the following description of exemplary embodiments with reference to the attached drawings.

BRIEF DESCRIPTION OF THE DRAWINGS

FIG. 2 is a diagram illustrating a hardware configuration of an imaging apparatus.

FIG. 3 is a diagram illustrating a hardware configuration of an image processing apparatus.

FIG. 4, including FIGS. 4A and 4B, is a flowchart illustrating processing of the image processing system.

FIG. 8, including FIGS. 8A and 8B, is a flowchart illustrating processing of an image processing system.

DESCRIPTION OF THE EMBODIMENTS

Exemplary embodiments of the disclosure will be described below with reference to the drawings.

Figure 1:
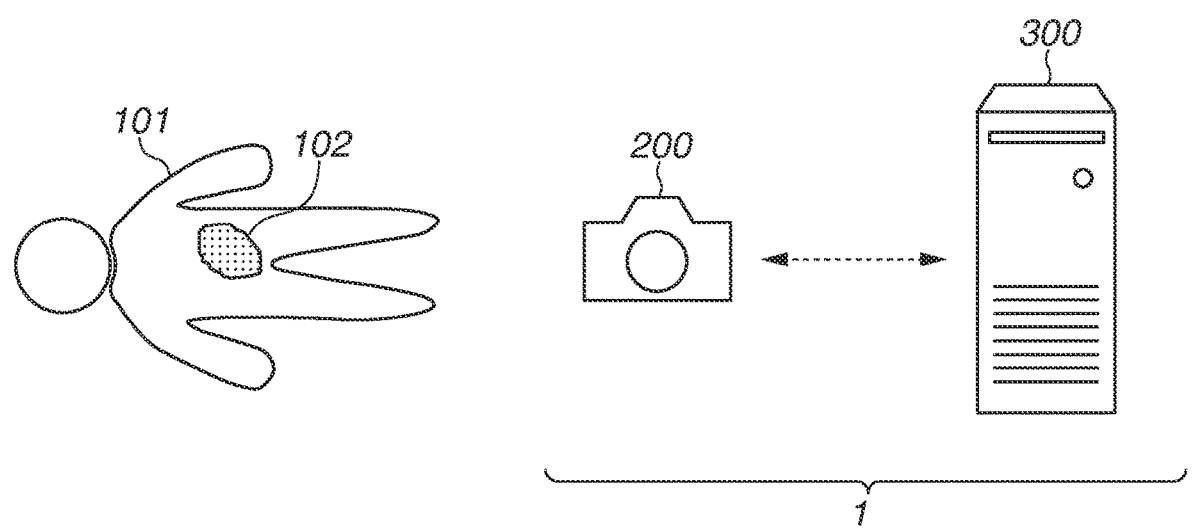
FIG. 1 is a diagram illustrating an outline of an image processing system.

FIG. 1 is a diagram illustrating an example of the outline of an image processing system according to a first exemplary embodiment.

The image processing system 1 includes an imaging apparatus 200 that is a handheld portable device, and an image processing apparatus 300. In the present exemplary embodiment, a pressure ulcer occurring on the buttocks will be described as an example of the condition of an affected part 102 of an object 101.

In the image processing system 1, the imaging apparatus 200 captures a live view image of the affected part 102 of the object 101, and transmits image data on the captured live view image to the image processing apparatus 300. The image processing apparatus 300 extracts an affected region including the affected part 102 from the received image data, calculates the area of the affected area, and transmits information about the calculated region to the imaging apparatus 200. If the received area of the affected region is greater than or equal to a threshold, the imaging apparatus 200 automatically captures an image of the affected part 102. While the present exemplary embodiment is described by using a case where the affected part 102 is a pressure ulcer as an example, the affected part 102 is not limited to pressure ulcers and may be burns or lacerations.

FIG. 2 is a diagram illustrating an example of a hardware configuration of the imaging apparatus 200.

The imaging apparatus 200 may be a standard single-lens camera, a compact digital camera, or a smartphone or tablet terminal including a camera having an autofocus function.

An imaging unit 211 includes a lens group 212, a shutter 213, and an image sensor 214. A focus position and a zoom magnification can be changed by changing the positions of a plurality of lenses included in the lens group 212. The lens group 212 also includes a diaphragm for adjusting an amount of exposure.

The image sensor 214 includes a solid-state image sensor of charge accumulation type for converting an optical image into image data. Examples of the solid-state image sensor include a charge-coupled device (CCD) sensor and a complementary metal-oxide-semiconductor (CMOS) sensor. Reflected light from the object 101, having passed through the lens group 212 and the shutter 213, forms an image on the image sensor 214. The image sensor 214 generates an electrical signal based on the object image, and outputs image data based on the generated electrical signal.

The shutter 213 exposes and shields the image sensor 214 to control an exposure time of the image sensor 214 by opening and closing blade members. The shutter 213 may be an electronic shutter that controls the exposure time by driving the image sensor 214. To implement an electronic shutter on a CMOS sensor, a reset scan for resetting the amount of charges accumulated in pixels to zero is performed pixel by pixel or in units of areas each including a plurality of pixels (for example, line by line). A scan for reading a signal based on the amount of accumulated charges is performed pixel by pixel or area by area each after a lapse of a predetermined time since the reset scan.

A zoom control circuit 215 controls a motor for driving a zoom lens included in the lens group 212 to control an optical magnification of the lens group 212.

A ranging system 216 calculates distance information about distance to the object 101. The ranging system 216 may use a typical phase difference ranging sensor included in a single lens reflex camera or a time-of-flight (TOF) sensor. A TOF sensor is a sensor that measures distance to an object based on a time difference (or phase difference) between transmission timing of an irradiation wave and reception timing of a reflected wave that is the irradiation wave reflected from the object. The ranging system 216 may use a position sensitive device (PSD) system where a PSD is used as a light reception element.

The image sensor 214 may be configured to include a plurality of photoelectric conversion regions in each pixel so that distance information at each pixel position or region position can be determined from a phase difference between images obtained by the respective photoelectric conversion regions.

The ranging system 216 may be configured to determine distance information in one or a plurality of predetermined ranging areas in an image. The ranging system 216 may be configured to determine a distance map indicating a distribution of distance information about a large number of pixels or areas in an image.

The ranging system 216 may perform television autofocusing (TV-AF) or contrast AF where high frequency components of image data are extracted and integrated to determine a position of the focus lens at which the integrated value is maximized. The ranging system 216 may obtain the distance information based on the position of the focus lens.

An image processing circuit 217 applies predetermined image processing to the image data output from the image sensor 214. The image processing circuit 217 performs various types of image processing, such as a white balance adjustment, gamma correction, color interpolation or demosaicing, and filtering, on the image data output from the imaging unit 211 or image data stored in an internal memory 221. The image processing circuit 217 also performs compression processing compliant with a Joint Photographic Experts Group (JPEG) standard on the image-processed image data.

An AF control circuit 218 determines the position of the focus lens included in the lens group 212 based on the distance information obtained by the ranging system 216, and controls a motor that drives the focus lens.

A communication unit 219 is a communication interface for communicating with an external apparatus, such as the image processing apparatus 300, via a wireless network. Specific examples of the network include a network based on a Wi-Fi (registered trademark) standard. The Wi-Fi based communication may be carried out via a router. The communication unit 219 may be implemented by a wired communication interface such as a Universal Serial Bus (USB) interface and a local area network (LAN).

A system control circuit 220 includes a central processing unit (CPU), and controls the entire imaging apparatus 200 by executing programs stored in the internal memory 221. The system control circuit 220 also controls the imaging unit 211, the zoom control circuit 215, the ranging system 216, the image processing circuit 217, and the AF control circuit 218. The system control circuit 220 is not limited to inclusion of the CPU, and may use a field programmable gate array (FPGA) or an application specific integrated circuit (ASIC). If predetermined imaging conditions are met, the system control circuit 220 generates internal signals similar to when a user issues an imaging instruction via an operation unit 224, based on the imaging conditions.

Rewritable memories such as a flash memory and a synchronous dynamic random access memory (SDRAM) can be used as the internal memory 221. The internal memory 221 temporarily stores various types of setting information such as information about a focus position during image capturing that is used for the operation of the imaging apparatus 200, image data captured by the imaging unit 211, and image data image-processed by the image processing circuit 217. The internal memory 221 may temporarily store image data and analytical data, such as information about the size of an object, that are received by the communication unit 219 through communication with the image processing apparatus 300.

An external memory 222 is a nonvolatile recording medium that is mountable on the imaging apparatus 200 or built in the imaging apparatus 200. Examples of the external memory 222 include a Secure Digital (SD) card and a CompactFlash (CF) card. The external memory 222 records image data image-processed by the image processing circuit 217, and image data and analytical data received by the communication unit 219 through communication with the image processing apparatus 300. During playback, the recorded image data can be read from the external memory 222 and output to outside the imaging apparatus 200.

Examples of a display unit 223 include a thin-film transistor (TFT) liquid crystal display, an organic electroluminescence (EL) display, and an electronic viewfinder (ENT). The display unit 223 displays the image data temporarily stored in the internal memory 221, the image data recorded in the external memory 222, and setting screens of the imaging apparatus 200.

The operation unit 224 includes buttons, switches, keys, and/or a mode dial arranged on the imaging apparatus 200, or a touch panel that also serves as the display unit 223. The user's commands such as mode setting commands and imaging instructions are notified to the system control circuit 220 via the operation unit 224.

A common bus 225 includes signal lines for transmitting and receiving between the components of the imaging apparatus 200.

FIG. 3 is a diagram illustrating an example of a hardware configuration of the image processing apparatus 300.

The image processing apparatus 300 includes a CPU 310, a storage unit 312, a communication unit 313, an output unit 314, and an auxiliary arithmetic unit 317.

The CPU 310 includes an arithmetic unit 311. The CPU 310 controls the entire image processing apparatus 300 by executing programs stored in the storage unit 312.

The storage unit 312 includes a main storage unit 315 (such as a read-only memory (ROM) and a random access memory (RAM)) and an auxiliary storage unit 316 (such as a magnetic disk drive and a solid state drive (SSD)).

The communication unit 313 is a wireless communication module for communicating with an external apparatus, such as the imaging apparatus 200, via a wireless network.

The output unit 314 outputs data processed by the arithmetic unit 311 and data stored in the storage unit 312 to a display, printer external network connected to the image processing apparatus 300.

The auxiliary arithmetic unit 317 is an integrated circuit (IC) for auxiliary operation that operates under control of the CPU 310. A graphics processing unit (GPU) may be used as the auxiliary arithmetic unit 317. A GPU, originally a processor for image processing, includes a plurality of multiplier-accumulators and is good at matrix calculation, and can thus also be used as a processor for signal learning processing. GPUs are therefore typically used for processing including deep learning. For example, the Jetson TX2 module manufactured by NVIDIA Corporation can be used as the auxiliary arithmetic unit 317. Alternatively, an FPGA or ASIC may be used as the auxiliary arithmetic unit 317. The auxiliary arithmetic unit 317 performs processing for extracting an affected region from image data.

The image processing apparatus 300 may include one or a plurality of CPUs 310 and one or a plurality of storage units 312. In other words, the image processing apparatus 300 implements functions to be described below when at least one or more CPUs and at least one or more storage units are connected and the at least one or more CPUs execute(s) programs stored in the at least one or more storage units. The image processing apparatus 300 is not limited to the CPU 310 and may use an FPGA or ASIC.

Figure 4B:
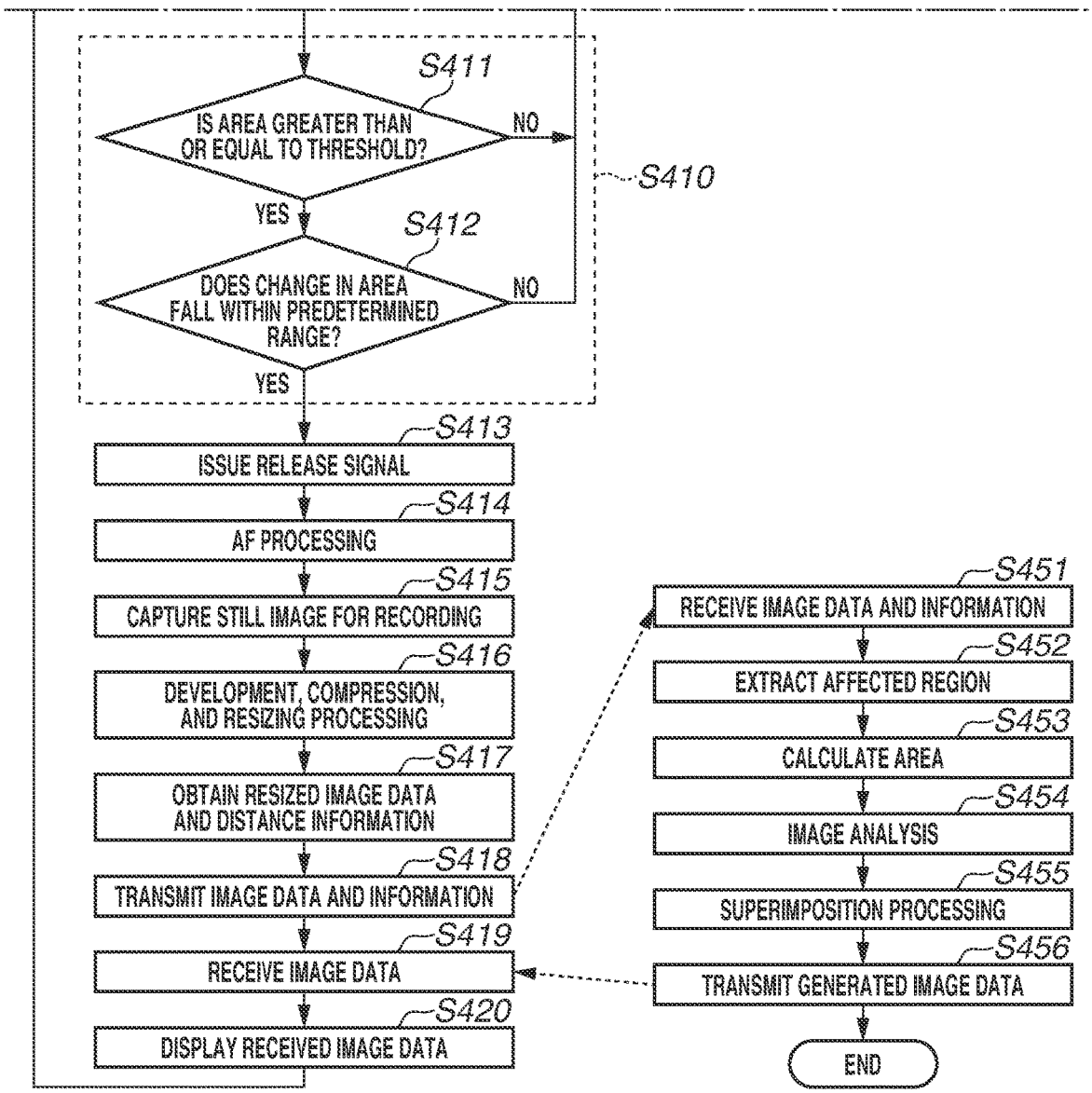

FIG. 4 consisting of FIGS. 4A and 4B is a flowchart illustrating an example of processing by the image processing system 1.

In FIGS. 4A and 4B, steps S401 to S420 represent processing by the imaging apparatus 200. Steps S431 to S456 represent processing by the image processing apparatus 300. The flowchart of FIGS. 4A and 4B is started by both the imaging apparatus 200 and the image processing apparatus 300 connecting to a network compliant with the Wi-Fi standard that is a wireless LAN standard.

In step S431, the image processing apparatus 300 performs search processing for searching for the imaging apparatus 200 to be connected.

In step S401, the imaging apparatus 200 performs response processing in response to the search processing by the image processing apparatus 300. Here, Universal Plug and Play (UPnP) is used as the technique for searching for a device over the network. In UPnP, each individual device is identified by a universally unique identifier (UM).

In step S402, the imaging apparatus 200 communicably connected to the image processing apparatus 300 starts live view processing. Specifically, the imaging unit 211 generates image data, and the image processing circuit 217 performs development processing for generating image data for a live view display on the generated image data. The imaging unit 211 and the image processing circuit 217 repeat the processing, whereby a live view image is displayed on the display unit 223 at a predetermined frame rate.

In step S403, the ranging system 216 determines distance information about the distance to the object 101, and the AF control circuit 218 starts AF processing for controlling driving of the lens group 212 so that the object 101 comes into focus. If the ranging system 216 adjusts the focus position by TV-AF or contrast AF, the ranging system 216 determines the distance information about the distance to the object 101 in the focused image based on the position of the focus lens in the in-focus state. The target to be brought into focus may be an object in the center of the image data or an object closest to the imaging apparatus 200. If the ranging system 216 has obtained a distance map about the object 101, the ranging system 216 may estimate a region of interest from the distance map and bring the estimated region into focus. If the position of the affected region in the live view image is already identified by the image processing apparatus 300, the ranging system 216 may bring the identified position into focus. The imaging apparatus 200 repeats the display of the live view image and the AF processing until a release signal is issued in step S413 to be described below.

In step S404, the image processing circuit 217 performs development and compression processing on one of the pieces of image data on the live view image to generate image data compliant with the JPEG standard, for example. The image processing circuit 217 performs resizing processing on the compressed image data to reduce the size of the image data.

In step S405, the communication unit 219 obtains the resized image data and the distance information determined by the ranging system 216. The communication unit 219 also obtains information about the zoom magnification and the size (number of pixels) of the resized image data as appropriate.

In step S406, the communication unit 219 transmits the obtained image data and one or more pieces of information including the distance information to the image processing apparatus 300 by wireless communication. The greater the size of the image data to be transmitted here, the longer the wireless communication takes. The system control circuit 220 thus determines the size into which the image processing circuit 217 resizes the image data in step S404 based on allowable communication time. If the size of the image data is too small, the accuracy of extraction processing to be described below where the image processing apparatus 300 extracts an affected region in step S442 can be affected. The system control circuit 220 therefore determines the size of the image data based on the accuracy of the extraction processing of the affected region in addition to the communication time. The processing of steps S404 to S406 may be performed frame by frame, or once in several frames.

The processing then proceeds to the processing by the image processing apparatus 300.

In step S441, the communication unit 313 of the image processing apparatus 300 receives the image data and the one or more pieces of information including the distance information transmitted from the communication unit 219 of the imaging apparatus 200.

In step S442, the CPU 310 and the auxiliary arithmetic unit 317 of the image processing apparatus 300 extract an affected region from the received image data.

Semantic segmentation based on deep learning is performed as a technique for extracting the affected region. Specifically, a high performance computer for training generates a trained model by training a neural network model with a plurality of images of affected regions of actual pressure ulcers as teaching data. The auxiliary arithmetic unit 317 obtains the trained model from the high performance computer, and estimates a pressure ulcer area, or affected region, from the image data based on the trained model. As an example of the neural network model, a fully convolutional network (FCN) that is a deep learning based segmentation model can be applied. Deep learning based estimation is processed by the auxiliary arithmetic unit 317 that is good at parallel execution of multiply-accumulate operations. However, the deep learning based estimation may be performed by an FPGA or ASIC. Other deep learning models may be used for segmentation. The segmentation technique is not limited to deep learning. For example, graph cut segmentation, region growing, edge detection, or divide-and-conquer segmentation may be used. The auxiliary arithmetic unit 317 may internally train a neural network model with images of affected regions of pressure ulcers as teaching data.

In step S443, the arithmetic unit 311 of the CPU 310 calculates the area of the affected region as information about the size of the extracted affected region.

Figure 5:
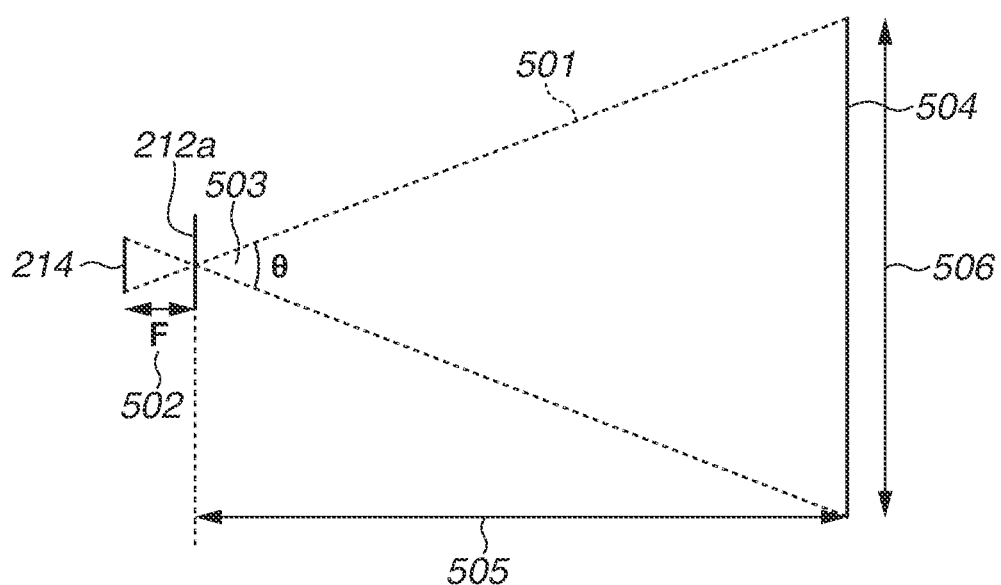
FIG. 5 is a diagram illustrating a method for calculating an area of an affected region.

FIG. 5 is a diagram illustrating a method for calculating the area of an affected region.

If the imaging apparatus 200 is a standard camera, the imaging apparatus 200 can be handled as a pinhole model as illustrated in FIG. 5. Incident light 501 passes through a principal point of a lens 212a and is received by the imaging surface of the image sensor 214. If the lens group 212 is approximated by a single lens 212a having no thickness, two principal points, i.e., the front and rear principal points, can be regarded as coinciding with each other. The imaging apparatus 200 can bring an object 504 into focus by adjusting the focus position of the lens 212a so that an image is formed on the plane of the image sensor 214. Changing a focal length 502 that is the distance F between the imaging surface and the lens principal point changes an angle of view θ 503, whereby the zoom magnification is changed. A width 506 of the object 504 on the in-focus plane is geometrically determined from the relationship between the angle of view θ 503 of the imaging apparatus 200 and an object distance 505. The width 506 of the object 504 is calculated by using a trigonometric function. Specifically, the width 506 of the object 504 is determined by the relationship between the angle of view θ 503, which changes with the focal length 502, and the object distance 505. A length on the in-focus plane corresponding to one pixel of the image data is obtained by dividing the width 506 of the object 504 by the number of pixels on a line of the image data.

The arithmetic unit 311 calculates the area of the affected region as the product of the number of pixels obtained from the affected region extracted in step S442 and an area per pixel determined from the length on the in-focus plane corresponding to one pixel of the image data. The length on the in-focus plane corresponding to one pixel of the image data may be determined in advance for various combinations of the focal length 502 and the object distance 505, and the resulting lengths may be provided as table data. Table data corresponding to various imaging apparatuses 200 may be stored in the image processing apparatus 300 in advance.

A precondition for the arithmetic unit 311 to correctly determine the area of the affected region is that the object 504 is a flat surface and the flat surface is perpendicular to the optical axis.

In step S444, the arithmetic unit 311 generates image data by superimposing information indicating the extraction result of the affected region and information about the size of the affected region on the image data from which the affected region is extracted (superimposition processing).

Figure 6A:
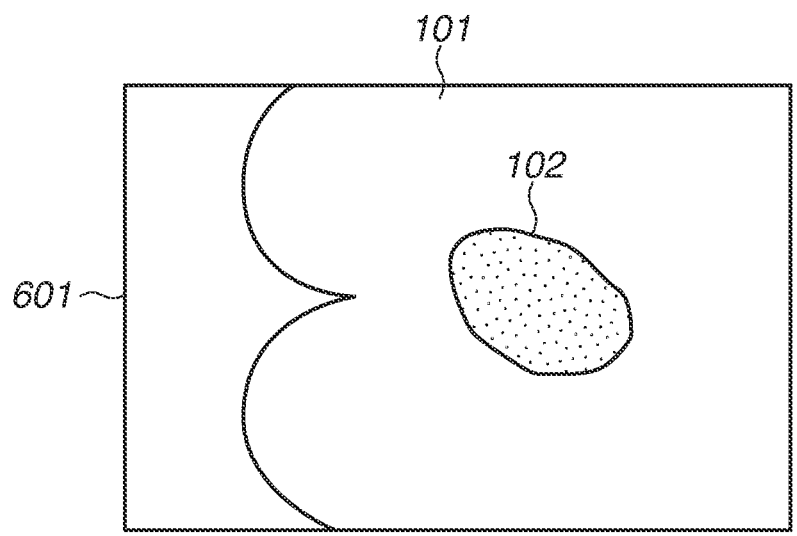
FIGS. 6A and 6B are diagrams illustrating a method for superimposing information upon image data on an affected part.
Figure 6B:
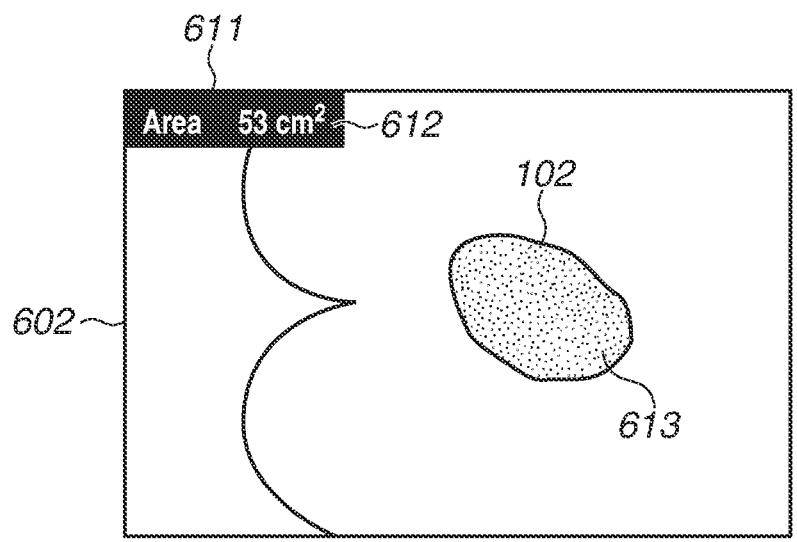

FIGS. 6A and 6B are diagrams illustrating a method for superimposing the information indicating the extraction result of the affected region and the information about the size of the affected region on the image data.

FIG. 6A illustrates an image 601 that is an example of image data displayed before the superimposition processing. The image 601 includes the object 101 and the affected part 102. FIG. 6B illustrates an image 602 that is an example of image data displayed after the superimposition processing.

A label 611 is superimposed on the top left corner of the image 602 illustrated in FIG. 6B. The label 611 displays a character string 612 indicating the area of the affected region in white characters on a black background. The information about the size of the affected region refers to the character string 612 and indicates the area of the affected region calculated by the arithmetic unit 311. The background color of the label 611 and the color of the character string 612 are not limited to black and while as long as easily viewable. Transparency may be set using a blending so that the user can observe the image where the label 611 overlaps.

An indicator 613 indicating the estimated area of the affected region extracted in step S442 is also superimposed on the image 602. The indicator 613 indicating the estimated area and the original image data of the image 601 are a blended so that the user can check whether the estimated area to calculate the area of the affected region from is appropriate. The color of the indicator 613 indicating the estimated area is desirably different from that of the object 101. The range of α blending transparency can be such that the estimated area can be distinguished from the original affected part 102. As long as the indicator 613 indicating the estimated area of the affected region is displayed in a superimposed manner, step S443 may be omitted since the user can check whether the estimated area is appropriate without the label 611.

In step S445, the communication unit 313 of the image processing apparatus 300 transmits the information indicating the extraction result of the affected region and the information about the size of the affected region to the imaging apparatus 200 by wireless communication. In the present exemplary embodiment, the communication unit 313 transmits the image data generated in step S444 and the area of the affected region, i.e., the information about the size of the affected region, to the imaging apparatus 200.

Next, the processing returns to the processing by the imaging apparatus 200.

In step S407, the communication unit 219 of the imaging apparatus 200 receives data transmitted from the image processing apparatus 300 if any.

In step S408, the system control circuit 220 determines whether the image data and the area of the affected region that is the information about the size of the affected region are received. If the image data and the area of the affected region are received (YES in step S408), the processing proceeds to step S409. If not (NO in step S408), the processing proceeds to step S410.

In step S409, the display unit 223 displays the received image data for a predetermined time. Here, the display unit 223 displays the image 602 illustrated in FIG. 6B. The superimposed display of the information indicating the extraction result of the affected region on the live view image enables the user (hereinafter, also referred to as a photographer) to check whether the area of the affected region and the estimated area are appropriate, before proceeding to image capturing for recording purposes. While in the present exemplary embodiment the indicator 613 indicating the estimated area of the affected region and the label 611 displaying the area of the affected region are described to be displayed, the display unit 223 may display either one of the indicator 613 and the label 611. The display unit 223 may be configured to display neither of the indicator 613 nor the label 611 (step S409 may be omitted).

In step S410, the system control circuit 220 controls timing to capture an image based on whether imaging conditions are satisfied. Step S410 includes steps S411 and S412. The area of the affected region is unable to be correctly calculated if the affected region is tilted with respect to the imaging apparatus 200. If the degree of tilt of the affected region with respect to the imaging apparatus 200 varies each time an image is captured, how the size changes is unable to be correctly determined when the captured images are compared afterward. Supporting a bedridden patient in the same position every time is difficult, and the photographer has difficulty in holding the imaging apparatus 200 to directly face the affected part. In steps S411 and S412, the imaging apparatus 200 therefore performs processing for estimating whether the imaging apparatus 200 is directly facing the affected region.

In step S411, the system control circuit 220 compares the received area of the affected region with a predetermined threshold, and determines whether the area is greater than or equal to the threshold. The threshold is recorded in the external memory 222 in advance as an initial value. The system control circuit 220 of the imaging apparatus 200 reads the threshold from the external memory 222 upon startup. For example, an area corresponding to a size at which an affected region is recognizable as a pressure ulcer is set as the threshold. The threshold can be freely changed and set by the user afterward. The threshold may thus be changed and set for each object to capture an image of. In step S411, if the area is not greater than or equal to the threshold (NO in step S411), the processing returns to step S404. The imaging apparatus 200 then performs the processing of step S404 and the subsequent steps described above.

In step S411, if the area is determined to be greater than or equal to the threshold (YES in step S411), the processing proceeds to step S412. In step S412, the system control circuit 220 determines a ratio or difference between the last received area and the area received immediately before the last. The last received area and the area received immediately before the last differ greatly while the photographer is moving the imaging apparatus 200 to situate the imaging apparatus 200 directly opposite the affected region. Specifically, as the imaging apparatus 200 in a state of being oblique to the affected region approaches a state of directly facing the affected region, the area of the affected region increases. On the other hand, as the imaging apparatus 200 in the state of directly facing the affected region approaches the state of being oblique to the affected region, the area of the affected region decreases. If the imaging apparatus 200 is in a state close to directly facing the affected region, a change in the area of the affected region decreases. In step S412, the system control circuit 220 determines whether the ratio or difference between the last received area and the area received immediately before the last falls within a predetermined range. If the ratio or difference between the last received area and the area received immediately before the last falls within the predetermined range, the system control circuit 220 therefore estimates that the imaging apparatus 200 is directly facing the affected region (YES in step S412) and the processing proceeds to step S413. In step S412, if the ratio or difference does not fall within the predetermined range (NO in step S412), the processing returns to step S404. The imaging apparatus 200 then performs the foregoing processing of step S404 and the subsequent steps.

In step S413, the system control circuit 220 issues a release signal. The release signal is a signal equivalent to one issued when the user presses the release button included in the operation unit 224 of the imaging apparatus 200 to issue an imaging instruction. The release signal is issued to emulate a situation where the release button is pressed by the user. In other words, the system control circuit 220 can issue the release signal at timing when the imaging apparatus 200 comes to a state close to directly facing the affected region while the photographer is moving the imaging apparatus 200 to situate the imaging apparatus 200 directly opposite the affected region.

In step S414, the ranging system 216 determines distance information about the distance to the object 101. The AF control circuit 218 performs the AF processing for controlling driving of the lens group 212 so that the object 101 comes into focus. This processing is similar to that of step S403. Since the AF processing is performed in step S403, the processing of step S414 here may be omitted.

In step S415, the imaging unit 211 captures a still image for recording at the timing of issuance of the release signal, and generates image data.

In step S416, the image processing circuit 217 performs development and compression processing on the generated image data to generate image data compliant with the JPEG standard, for example. The image processing circuit 217 performs resizing processing on the compressed image data to reduce the size of the image data. To give priority to the accuracy in measuring the affected region, the size of the image data resized here is desirably greater than or equal to that of the image data resized in step S404. For example, resized 4-bit red-green-blue (RGB) color image data including 1440×1080 pixels has a size of approximately 4.45 megabytes. However, the size of the resized image data is not limited thereto.

In step S417, the communication unit 219 obtains the resized image data and the distance information obtained by the ranging system 216 in step S414. The communication unit 219 also obtains information about the zoom magnification and information about the size (number of pixels) of the resized image data as appropriate.

In step S418, the communication unit 219 transmits the obtained image data and one or more pieces of information including the distance information to the image processing apparatus 300 by wireless communication.

Next, the processing by the image processing apparatus 300 will be described.

In step S451, the communication unit 313 of the image processing apparatus 300 receives the image data and the one or more pieces of information including the distance information transmitted from the communication unit 219 of the imaging apparatus 200.

In step S452, the CPU 310 and the auxiliary arithmetic unit 317 of the image processing apparatus 300 extract the affected region from the received image data. Details of this processing are similar to those of step S442. A description thereof will thus be omitted.

In step S453, the arithmetic unit 311 of the CPU 310 calculates the area of the affected region as information about the size of the extracted affected region. Details of this processing are similar to those of step S443. A description thereof will thus be omitted.

In step S454, the arithmetic unit 311 performs image analysis. Specifically, the arithmetic unit 311 calculates the lengths of the major and minor axes of the extracted affected region and the area of a rectangle circumscribing the affected region based on the length on the in-focus plane corresponding to one pixel of the image data obtained in step S453. The pressure ulcer evaluation index DESIGN-R defines that the size of a pressure ulcer is measured as the value of the product of the lengths of the major and minor axes. By analyzing the major and minor axes, the image processing system 1 according to the present exemplary embodiment can secure compatibility with data measured according to DESIGN-R. Since DESIGN-R does not include a definition of a method for mathematically calculating the major and minor axes, there can be a plurality of possible methods according to DESIGN-R.

As a first example of the method for calculating the major and minor axes, the arithmetic unit 311 calculates a rectangle (minimum bounding rectangle) having the smallest area among rectangles circumscribing the affected region. The arithmetic unit 311 then calculates the lengths of the long and short sides of the rectangle as the major axis and the minor axis, respectively. The arithmetic unit 311 calculates the area of the rectangle based on the length on the in-focus plane corresponding to one pixel of the image data obtained in step S453.

As a second example of the method for calculating the major and minor axes, the arithmetic unit 311 selects a maximum Feret diameter that is the maximum caliper diameter as the major axis, and selects a minimum Feret diameter as the minor axis. The arithmetic unit 311 may select the maximum Feret diameter that is the maximum caliper diameter as the major axis, and selects a length measured in a direction orthogonal to the axis of the maximum Feret diameter as the minor axis.

Any method for calculating the major and minor axes can be selected based on compatibility with conventional measurement results.

The processing for calculating the lengths of the major and minor axes of the affected region and the area of the rectangle is not performed on the image data received in step S441. The live view is intended to allow the user to check the extraction result of the affected region. The image analysis processing corresponding to step S454 on the image data received in step S441 is thus omitted to reduce the processing time.

In step S455, the arithmetic unit 311 generates image data by superimposing information indicating the extraction result of the affected region and information about the size of the affected region on the image data from which the affected region is extracted.

Figure 7A:
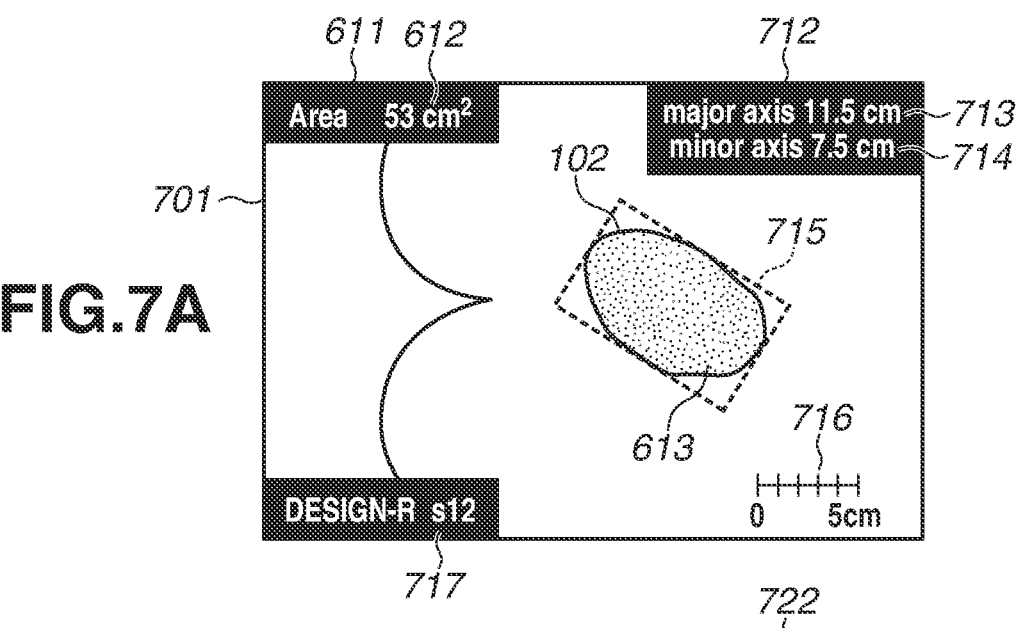
FIGS. 7A, 7B, and 7C are diagrams illustrating a method for superimposing information upon the image data on the affected part.
Figure 7B:
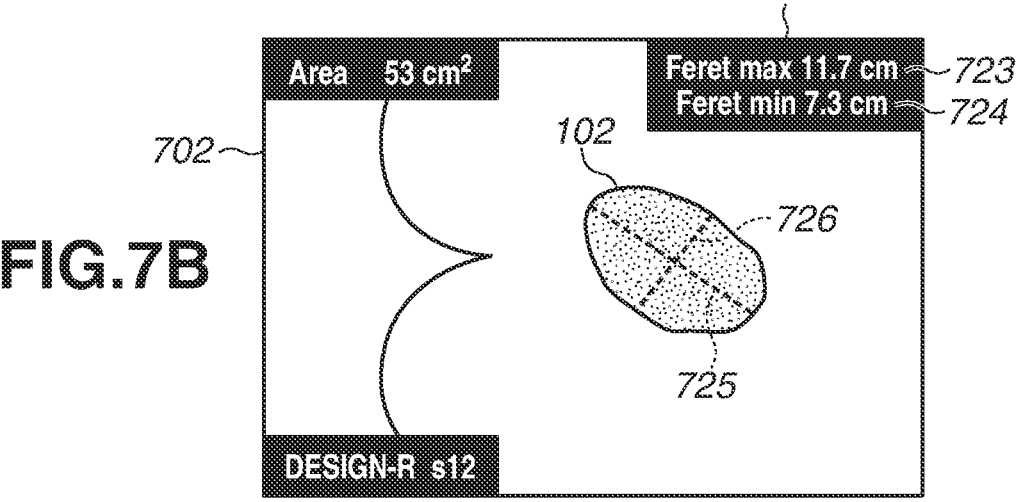
Figure 7C:
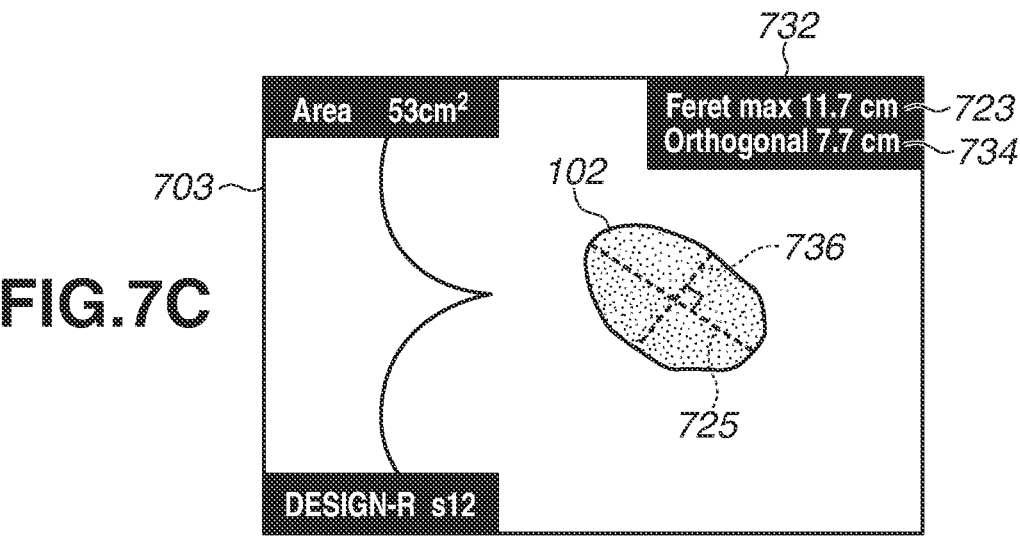

FIGS. 7A to 7C are diagrams illustrating a method for superimposing the information indicating the extraction result of the affected region and the information about the size of the affected region including the major and minor axes of the affected region on the image data. Since a plurality of types of information about the size of the affected region can be assumed, respective methods will be described with reference to FIGS. 7A to 7C.

FIG. 7A illustrates an image 701 that is generated by using a minimum bounding rectangle as the method for calculating the major and minor axes. Like FIG. 6B, the label 611 displaying the character string 612 indicating the area of the affected region in white characters on the black background is superimposed on the top left corner of the image 701 as the information about the size of the affected region.

A label 712 displaying the major and minor axes calculated based on the minimum bounding rectangle is superimposed on the top right corner of the image 701 as information about the size of the affected region. The label 712 includes character strings 713 and 714. The character string 713 indicates the length of the major axis (in units of cm). The character string 714 indicates the length of the minor axis (in units of cm). A rectangular frame 715 representing the minimum bounding rectangle is superimposed on the affected region in the image 701. The superimposition of the rectangular frame 715 along with the lengths of the major and minor axes allows the user to check the measurement positions where the lengths are measured in the image 701.

A scale bar 716 is superimposed on the bottom right corner of the image 701. The scale bar 716 is intended to measure the size of the affected part 102. The size of the scale bar 716 with respect to the image data is changed based on the distance information. Specifically, the scale bar 716 is a bar graduated up to 5 cm in units of 1 cm based on the length on the in-focus plane corresponding to one pixel of the image data obtained in step S453, and corresponds to size on the in-focus plane of the imaging apparatus 200, i.e., on the object 101. The user can figure out the size of the object 101 or the affected part 102 by referring to the scale bar 716.

A size evaluation index 717 according to the foregoing DESIGN-R is superimposed on the bottom left corner of the image 701. As described above, there are seven classification grades of the size evaluation index 717 according to DESIGN-R, based on the numerical value obtained by measuring the major axis and the minor axis (maximum diameter orthogonal to the major axis) (in units of cm) of the skin wound area and multiplying the measurements. In the present exemplary embodiment, a size evaluation index 717 obtained by replacing the major and minor axes with values output by respective calculation methods is superimposed.

FIG. 7B illustrates an image 702 that is generated by using the maximum Feret diameter as the major axis and the minimum Feret diameter as the minor axis. A label 722 displaying a character string 723 indicating the length of the major axis and a character string 724 indicating the length of the minor axis is superimposed on the top right corner of the image 702. An auxiliary line 725 representing the measurement position of the maximum Feret diameter and an auxiliary line 726 representing the measurement position of the minimum Feret diameter are displayed in the affected region in the image 702. The superimposition of the auxiliary lines 725 and 726 along with the character strings 723 and 724 indicating the lengths of the major and minor axes allows the user to figure out the measurement positions where the lengths are measured in the image 702.

FIG. 7C illustrates an image 703 where the major axis is the same as the image 702 illustrated in FIG. 7B and the minor axis is obtained by measuring not the minimum Feret diameter but a length in the direction orthogonal to the axis of the maximum Feret diameter. A label 732 displaying the character string 723 indicating the length of the major axis and a character string 734 indicating the length of the minor axis is superimposed on the top right corner of the image 703. The auxiliary line 725 corresponding to the measurement position of the maximum Feret diameter and an auxiliary line 736 corresponding to the length measured in the direction orthogonal to the axis of the maximum Feret diameter are displayed in the affected region in the image 703.

Each of the various types of information on the image data illustrated in FIGS. 7A to 7C may be superimposed singly, or a plurality of types of information may be superimposed in combination. The user may be able to select information to be displayed. The images illustrated in FIGS. 6A and 6B and 7A to 7C are merely examples. The display mode, display positions, sizes, fonts, font sizes, font colors, and positional relationship of the information about the affected part 102 and the size of the affected region may be modified based on various conditions.

In step S456, the communication unit 313 of the image processing apparatus 300 transmits the information indicating the extraction result of the affected region and the information about the size of the affected region to the imaging apparatus 200. In the present exemplary embodiment, the communication unit 313 transmits the image data generated in step S455 to the imaging apparatus 200.

The processing then proceeds to the processing by the imaging apparatus 200.

In step S419, the communication unit 219 of the imaging apparatus 200 receives the image data transmitted from the image processing apparatus 300.

In step S420, the display unit 223 displays the received image data for a predetermined time. Here, the display unit 223 displays one of the images 701 to 703 illustrated in FIGS. 7A to 7C. After a lapse of the predetermined time, the processing returns to step S402.

As described above, according to the present exemplary embodiment, the system control circuit 220 controls the timing to capture an image of the affected part 102 based on the obtained information about the size of the affected region. Since the system control circuit 220 can control imaging of the affected part to be automatically executed when the imaging apparatus 200 is situated so that the size of the affected region is appropriate, an image of the affected part 102 can be appropriately captured even if the user is positioned in an unnatural posture in capturing the image.

Specifically, the system control circuit 220 controls imaging of the affected part 102 to be automatically executed by issuing the release signal if a received new area of the affected region is greater than or equal to a threshold and a change between the received new area of the affected region and the area of the affected region received immediately before falls within a predetermined range. In other words, if the area of the affected region is greater than or equal to the threshold, the imaging apparatus 200 can be assumed to be in an appropriate position to capture an image of the affected part 102. If a change in the area of the affected region falls within the predetermined range, the imaging apparatus 200 can be assumed to be in a state close to directly facing the affected region. The user can thus appropriately capture an image of the affected part 102 since the system control circuit 220 controls the imaging of the affected part to be automatically executed when such conditions are satisfied. Alternatively, the imaging apparatus 200 may be configured to determine that the imaging apparatus 200 is in an appropriate position to capture an image of the affected part 102 by determining only whether a change in the area of the affected region falls within the predetermined range, without determining whether the area of the affected region is greater than or equal to the threshold.

The processing for displaying the image data in the foregoing step S409 is performed if the user manually gives imaging instructions. If the system control circuit 220 issues the release signal, step S409 may be omitted. Similarly, the processing for generating the superimposed image data in step S444 may be omitted. In step S445, the information about the size of the affected region may be transmitted without the image data.

In the image processing system 1 according to the present exemplary embodiment, the information about the size of the affected region is displayed on the display unit 223 of the imaging apparatus 200 by the user capturing an image of the affected part 102 with the imaging apparatus 200. This can reduce the burden on the medical personnel and the burden on the patient to be evaluated in evaluating the size of the affected region of the pressure ulcer. Since the size of the affected region is calculated based on a computer program, individual differences can be reduced and the accuracy of the size evaluation on the pressure ulcer can be improved compared to when the medical personnel manually measures the size. In addition, the area of the affected region serving as an index for indicating the scale of the pressure ulcer more accurately can be calculated and displayed. The function by which the user checks whether the estimated area of the affected region is appropriate during a live view display is dispensable, and steps S441 to S445 may be omitted.

The image processing apparatus 300 may store the information indicating the extraction result of the affected region, the information about the size of the affected region, and the image data on which such pieces of information are superimposed in the storage unit 312. In such a case, the output unit 314 can output any one or more pieces of information or image data stored in the storage unit 312 to a connected output device such as a display. The image display on the display allows a user other than the one who captures the image of the affected part 102 to obtain the image data on the affected part 102 and the information about the size in real time or those obtained in the past. The arithmetic unit 311 of the image processing apparatus 300 may have a function of displaying scale bars for freely changing position and angle on the image data transmitted from the output unit 314 to the display. Displaying such scale bars allows the user viewing the display to measure the lengths of desired positions of the affected region. The graduations on the scale bars are automatically adjusted based on the distance information received in step S451, the information about the zoom magnification, and the information about the size (number of pixels) of the resized image data.

The image processing apparatus 300 can be a stationary device with constant supply of power. The constant supply of power enables the image processing apparatus 300 to receive image data on affected parts and information about size at any timing, and can prevent a dead battery. Since stationary devices typically have a large storage capacity, the image processing apparatus 300 of stationary type can store a large number of pieces of image data.

(First Modification)

In the flowchart of FIGS. 4A and 4B described above, if the area is determined to not be greater than or equal to the threshold in step S411, the processing does not proceed to step S412 and the processing of step S404 and the subsequent steps is repeated. However, the affected region does not necessarily have a specific size or more. If the determination in step S411 of the flowchart of FIG. 4B is NO, the system control circuit 220 may therefore determine whether a certain period has elapsed in the state where the area is not greater than or equal to the threshold. If the certain period has not elapsed, the processing returns to step S404. If the certain period has elapsed, the system control circuit 220 estimates that the size of the affected region is small, and the processing proceeds to step S412. For example, the certain period may be defined based on a time period, such as 5 sec and 10 sec. The certain period may be defined based on the number of times of data reception in step S408. By issuing the release signal when the certain time has elapsed, the imaging apparatus 200 can capture an image of the affected part 102 even if the affected region does not have a certain size or more.

(Second Modification)

In the flowchart of FIGS. 4A and 4B described above, the processing of step S410 is described to control the imaging timing based on whether the imaging conditions are satisfied. However, the processing may control timing to prompt the user to perform an imaging operation based on whether the imaging conditions are satisfied. Specifically, if the processing proceeds from step S412 to step S413, the system control circuit 220 may issue a notification prompting the user to perform an imaging operation. For example, the system control circuit 220 prompts the user to press the release button included in the operation unit 224 by issuing a notification by voice or an alarm, or displaying a notification on the display unit 223. According to this modification, after step S413, the system control circuit 220 determines whether the release button included in the operation unit 224 is actually pressed by the user. If the released button is pressed, the processing proceeds to step S414.

A second exemplary embodiment will be described below. In the first exemplary embodiment, the threshold to be compared with the area of the affected region is described to be determined in advance. The present exemplary embodiment describes a case where history information is used as the threshold. In the following description, similar components to those of the first exemplary embodiment are designated by the same reference numerals. A detailed description thereof will be omitted.

Specifically, in step S411, the system control circuit 220 compares the received area of the affected region with a predetermined threshold. If the area is greater than or equal to the threshold, the processing proceeds to step S412. In step S412, if a change in the area falls within a predetermined range, the processing proceeds to step S413. In step S413, the system control circuit 220 issues the release signal, and records the received area in the external memory 222. If the processing of the flowchart of FIGS. 4A and 4B proceeds to step S411 in capturing an image of the affected part 102 next time, the system control circuit 220 reads the area recorded in the external memory 222 as the threshold. The system control circuit 220 may determine a threshold by setting a margin for the read threshold. For example, the system control circuit 220 may determine a threshold by subtracting a specific margin from the read threshold. The longer the interval from the previous imaging, the greater margin may be subtracted from the read threshold.

In recording the area, the system control circuit 220 can record the area to be recorded and patient information in association with each other. For example, the imaging apparatus 200 or the image processing apparatus 300 can obtain patient information by the user inputting or selecting the patient information into/on the imaging apparatus 200 or the image processing apparatus 300. If the image processing apparatus 300 obtains patient information, then in step S445, the image processing apparatus 300 transmits the patient information to the imaging apparatus 200 in association with the area. This enables the imaging apparatus 200 to record the area and the patient information in association with each other.

If patient information is used, the system control circuit 220, in step S411, reads the area associated with the patient information as a threshold, and compares the threshold with the received area. If the area is greater than or equal to the threshold (YES in step S411), the processing proceeds to step S412, in step S412, if a change in the area falls within a predetermined range (YES in step S412), the processing proceeds to step S413. In step S413, the system control circuit 220 issues the release signal, associates the received area with the patient information, and records the received area for update. If there is no area associated with the patient information, the system control circuit 220 either compares a predetermined threshold (initial value) with the received area or displays a notification prompting the user to manually capture an image on the display unit 223.

The image processing apparatus 300 may record the area in association with the patient information. For example, suppose that the imaging apparatus 200 captures a barcode tag including patient information about the patient before capturing the affected part 102. The imaging apparatus 200 transmits the image data on the barcode tag to the image processing apparatus 300 during transmission in the foregoing step S406. The image processing apparatus 300 obtains the patient information from the image data on the barcode tag, reads the area associated with the patient information as a threshold, and transmits the threshold to the imaging apparatus 200 during transmission in the foregoing step S445. The system control circuit 220 of the imaging apparatus 200 can thus set the threshold corresponding to the patient by controlling the imaging timing based on the received threshold. The CPU 310 of the image processing apparatus 300 may further update the area recorded in association with the patient information with the area of the affected region calculated in step S453.

As described above, according to the present exemplary embodiment, the threshold is set based on the area of the affected region captured in the past, and compared with the received area. Since the size of a pressure ulcer usually changes over time, the imaging apparatus 200 can capture an image of the affected part under appropriate conditions by setting the threshold based on the area of the affected region captured in the past. The imaging apparatus 200 can also capture an image of the affected part under optimum conditions corresponding to the patient by setting the threshold based on the area of the affected region of the same patient captured in the past. Since the accuracy of the threshold improves, the imaging apparatus 200 may be configured so that if the area of the affected region is greater than or equal to the threshold in step S411, the processing skips step S412 and proceeds to step S413 to issue the release signal.

A third exemplary embodiment will be described below. In the first exemplary embodiment, if a change in the area of an affected region is within a predetermined range, the imaging apparatus 200 is determined to be directly facing the affected region. The present exemplary embodiment describes a case where it is determined whether an imaging apparatus 200 is directly facing an object including an affected part by using distance information. If the imaging apparatus 200 is directly facing the object, a release signal is issued. In the following description, similar components to those of the first exemplary embodiment are designated by same reference numerals. A detailed description thereof will be omitted.

Figure 8B:
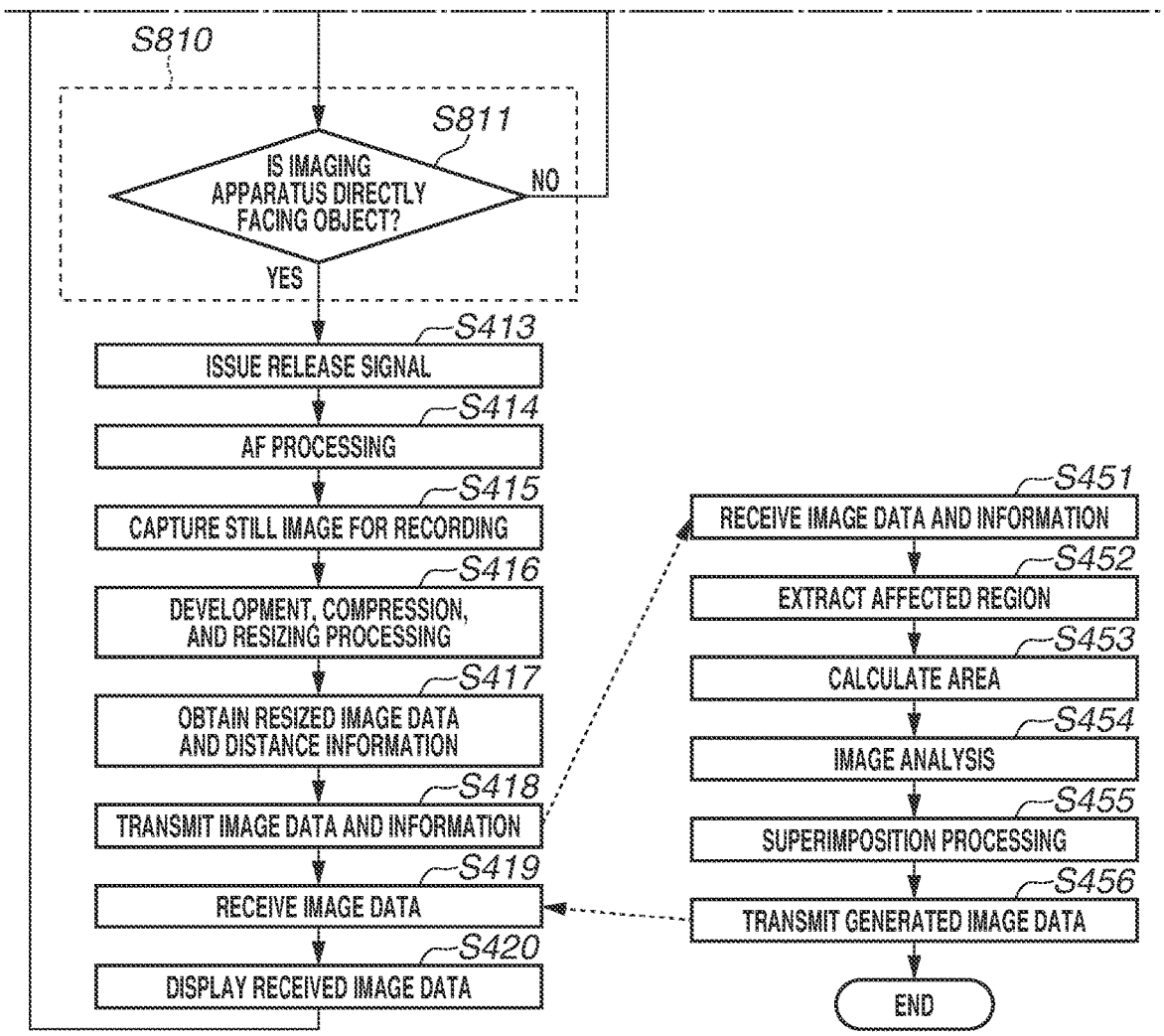

FIG. 8 consisting of FIGS. 8A and 8B is a flowchart illustrating an example of processing by the image processing system 1. Similar processing to that of FIGS. 4A and 4B are designated by the same step numbers, and a description thereof will be omitted as appropriate. Specifically, the flowchart of FIGS. 8A and 8B is obtained by replacing step S410 in the flowchart of FIG. 4B with step S810.

Step S810 represents processing where the system control circuit 220 controls the timing to capture an image based on the orientation of the imaging apparatus 200 with respect to the object. Step S810 includes steps S811.

In step S811, the system control circuit 220 determines whether the imaging apparatus 200 is directly facing the object including the affected part. As described above, the ranging system 216 of the imaging apparatus 200 can calculates distance information about the distance to the object or a distance map (distance map information) indicating a distribution of distance information. Information about a plane can be obtained by using distance information or distance map information about three or more points. If the pieces of distance information about the respective points coincide with each other or have less than a predetermined difference, the object and the imaging apparatus 200 can be determined to be directly facing each other.

The system control circuit 220 can thus determine whether the imaging apparatus 200 is directly facing the object based on the distance information or distance map information calculated by the ranging system 216. If the imaging apparatus 200 is determined to be directly facing the object (YES in step S811), the processing proceeds to step S413. In step S413, the system control circuit 220 issues a release signal. If the imaging apparatus 200 is determined to be not directly facing the object (NO in step S811), the processing returns to step S404.

As described above, according to the present exemplary embodiment, the timing to capture an image is controlled based on the orientation of the imaging apparatus 200 with respect to the object. Since the release signal can be issued when the imaging apparatus 200 is directly facing the object, an image of the affected part can be appropriately captured.

Various exemplary embodiments and modifications of the disclosure have been described above. However, the disclosure is not limited to the foregoing exemplary embodiments and modifications, and various modifications can be made without departing from the scope of the disclosure. The foregoing exemplary embodiments and modifications may be combined as appropriate.

For example, the first exemplary embodiment may be combined with the third exemplary embodiment. Specifically, the system control circuit 220 may determine whether the imaging apparatus 200 is directly facing the object based on the distance information, and if the imaging apparatus 200 is determined to be directly facing the object, compare the received area with the threshold. If the area is greater than or equal to the threshold, the system control circuit 220 may issue the release signal. Alternatively, the system control circuit 220 may determine whether the received area is greater than or equal to the threshold, and if the area is greater than or equal to the threshold, determine whether the imaging apparatus 200 is directly facing the object based on the distance information, lithe imaging apparatus 200 is directly facing the object, the system control circuit 220 may issue the release signal.

In the foregoing exemplary embodiments, the information about the size of the affected region is described to be the area of the affected region. However, this is not restrictive, and the information about the size of the affected region may be any one of the following: the area of the affected region, the length of the major axis of the affected region, and the length of the minor axis of the affected region. If the length of the major axis of the affected region or the length of the minor axis of the affected region is used as the information about the size of the affected region, the system control circuit 220 obtains, in step S408, the length of the major axis of the affected region or the length of the minor axis of the affected region. In step S411, the system control circuit 220 can determine whether the length of the major axis of the affected region or the length of the minor axis of the affected region is greater than or equal to a predetermined threshold.

In the foregoing exemplary embodiments, the imaging apparatus 200 is described to include the system control circuit 220. However, this is not restrictive. The imaging apparatus 200 may not include the system control circuit 220, in which case the processing to be performed by the system control circuit 220 is executed by various hardware circuits.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Applications No. 2019-045955, filed Mar. 13, 2019, and No. 2020-023378, filed Feb. 14, 2020, which are hereby incorporated by reference herein in their entirety.

What is claimed is:

1. A handheld apparatus comprising:
an image sensor; an image processing circuit that generates a live view image from image data generated using the image sensor; and a processor that acquires information on a size of an area of an affected part, of a patient, extracted from image data included in the live view image, wherein the processor performs control such that a still image is captured in a case where the processor determines that predetermined conditions are satisfied in the live view image, and wherein the predetermined conditions include that a ratio or a difference between a last received area of the affected part and an area of the affected part received before a last falls within a predetermined range, and wherein the predetermined conditions further include that the size of the affected part is greater than or equal to a threshold, and wherein the threshold is a value based on a size of the affected part of a same patient which has been captured before.

2. The apparatus according to claim 1, wherein the processor performs control such that a still image is not captured in a case where the predetermined conditions are not satisfied in the live view image.

3. The apparatus according to claim 1, wherein the processor is configured to, if the size of the affected part is not greater than or equal to the threshold and a predetermined period has elapsed, control the capturing the still image.

4. The apparatus according to claim 1, wherein the processor is configured to transmit the image data included in the live view images to an outside via a communication circuit, and receive information about the size of the affected part from the outside via the communication circuit in response to transmission of the image data included in the live view images to the outside.

5. The apparatus according to claim 4, wherein the processor is configured to receive the information about the size of the affected part via the communication circuit each time the image data included in the live view images is transmitted to the outside via the communication circuit.

6. The apparatus according to claim 1,
wherein the affected part is a pressure ulcer, and
wherein the size of the affected part is at least any one of the following: an area of an affected region, a length of a major axis of the affected region, and a length of a minor axis of the affected region.

7. A method comprising:
generating a live view image from image data generated using an image sensor;
acquiring information on a size of an area of an affected part, of a patient, extracted from image data included in the live view image; and
performing control such that a still image is captured in a case where it is determined that predetermined conditions are satisfied in the live view image,
wherein the predetermined conditions include that a ratio or a difference between a last received area of the affected part and an area of the affected part received before a last fall within a predetermined range,
and wherein the predetermined conditions further include that the size of the affected part is greater than or equal to a threshold, and wherein the threshold is a value based on a size of the affected part of a same patient which has been captured before.

8. The method according to claim 7, further comprising:
transmitting the image data included in the live view images to an outside via a communication circuit; and
receiving information about the size of the affected part from the outside via the communication circuit in response to transmission of the image data included in the live view images to the outside.

* * * * *